United States Patent [19]

Vanderstraeten

[11] Patent Number: 5,925,458

[45] Date of Patent: Jul. 20, 1999

[54] PROCESS FOR THE PREPARATION OF PROSTHESES FOR SKELETAL RECONSTRUCTION

[75] Inventor: Johan Emile Marie Vanderstraeten, Drongen, Belgium

[73] Assignee: COATINVEST, Drongen, Belgium

[21] Appl. No.: 09/086,521

[22] Filed: May 29, 1998

Related U.S. Application Data

[62] Division of application No. 08/676,628, Jul. 10, 1996, Pat. No. 5,789,017.

[30] Foreign Application Priority Data

Jul. 12, 1995 [GB] United Kingdom .................. 9514224

[51] Int. Cl.$^6$ ....................................................... B32B 5/16
[52] U.S. Cl. .......................... 428/341; 428/323; 428/332; 428/336; 428/338; 428/341; 428/408; 623/11; 623/16
[58] Field of Search .................................. 428/323, 332, 428/336, 338, 341, 408; 623/11, 16

[56] References Cited

PUBLICATIONS

Degroot, CRC Press Inc., Plasma Sprayed Caoting of Calcium Phosphate, 1990.

*Primary Examiner*—Richard Weisberger
*Attorney, Agent, or Firm*—Bacon & Thomas, PLLC

[57] ABSTRACT

A process for the coating of a carbon fiber composite which comprises carbon fibers bonded together with a polymeric material, which process comprises positioning the carbon fiber composite in a chamber maintained at a reduced pressure of from 25,000 to 10,000 Pa (250 to 100 mBar), and plasma spraying a coating onto a surface of the carbon fiber composite whilst cooling the said surface of the composite with an inert liquid coolant medium the said coating composition being selected from the group consisting of non-agglomerated hydroxyapatite or non-agglomerated modified hydroxyapatite.

12 Claims, No Drawings

PROCESS FOR THE PREPARATION OF PROSTHESES FOR SKELETAL RECONSTRUCTION

CROSS REFERENCE TO RELATED APPLICATIONS

This application is a divisional application of application Ser. No. 08/676,628, filed Jul. 10, 1996, which has been allowed, now U.S. Pat. No. 5,789,017.

The present invention relates to a process for the preparation of prostheses for skeleton reconstruction and in particular, to the preparation of prostheses which are based on carbon fibers.

BACKGROUND OF THE INVENTION

The most frequent use of prostheses for skeleton reconstruction involves the total replacement of articulating joints which have been rendered nonfunctional, either by physical accident (trauma) or, more commonly, by one of several kinds of arthritis. The total prosthetic replacement of hip joints and knee joints is now widespread and there are also surgical procedures and prosthesis designs for the reconstruction of other joint systems, such as ankle, shoulder, finger, wrist and elbow joints.

The load bearing requirements of prostheses for skeletal reconstruction, especially in the lower limb, imposes special performance demands on the materials of construction. The joint replacement systems which have been most extensively used heretobefore involve a metal component, such as titanium and a polymer component which is coated onto one or both of the articulating surfaces of the joint. The polymer is preferably an ultrahigh molecular weight polyethylene which is both biocompatible and very resistant to wear. The parts of the prostheses which are implanted into the bone may be fixed in position with bone cement. More recently, however, it has been found that coating the parts of the prosthesis which are to be implanted into the bone with hydroxyapatite or a modified hydroxyapatite will host the growth of bone into the coating and thus assist in anchoring the implant in position. Hydroxyapatite is a member of the apatite group of minerals and has the chemical formula $Ca_{10}(PO_4)_6(OH)_2$. It is, essentially, a calcium phosphate including hydroxide having a Ca/P ratio of 1.67. Synthetic hydroxyapatite has the chemical structure given above and is similar structurally to bone material which thus makes it an ideal coating material for prostheses. Synthetic hydroxyapatite may be modified, for example, by substitution at the phosphate and hydroxyl sites, for example by carbonate groups.

The coating of implants with hydroxyapatite is described in a paper entitled "Contribution of Hydroxyapatite Coatings to Implant Fixation", by E. Munting, M. Verhelpen, Feng Li and A. Vincent from CRC Handbook of Bioactive Ceramics Volume II. Calcium Phosphate and Hydroxyapatite Ceramics, CRC Press Inc (1990).

The coating of the portions of the prostheses which are implanted into the bone with hydroxyapatite or a modified hydroxyapatite is carried out by well known techniques, for example by plasma spraying or sputtering. The plasma spray coating of hydroxyapatite is described in "Plasma Sprayed Coatings of Calcium Phosphate" by K. DeGroot, C. P. A. T. Klein, J. G. C. Wolke and J. M. A. de Bliek-Hagervorst from CRC Handbook of Bioactive Ceramics Volume II. Calcium Phosphate and Hydroxyapatite Ceramics, CRC Press Inc. (1990).

Low pressure plasma spraying of hydroxyapatite is generally preferred for the coating of prostheses. Using this technique the hydroxyapatite is injected into the plasma flame of a plasma gun where it melts. As the plasma steam impinges upon the substrate surface the hydroxyapatite in the plasma stream crystallizes and solidifies to form a hydroxyapatite coating.

Although for many applications titanium or other metal prostheses are satisfactory, they suffer from the disadvantage that they are relatively heavy, have a high Young's Modulus and require a surface roughening treatment prior to coating, such as by grit blasting, with the consequent difficulty of complete removal of debris following such a treatment. Accordingly, it has been suggested that prostheses should be based upon carbon fibers which are biocompatible, inert and strong. The carbon fibers require, however, to be bonded together into a composite of the desired shape for the prosthesis by using a synthetic polymer such as polybutyleneterephthalate. An acetabulum for a total hip prosthesis, which may be made from a carbon fiber reinforced plastics material is described in EP-A-0552949.

The plasma spraying of hydroxyapatite onto carbon fiber reinforced thermoplastic composite materials is disclosed in a paper entitled "Plasma-sprayed hydroxylapatite coating on carbon fiber reinforced thermoplastic composite materials", by S. -W. Ha, J. Mayer, B. Koch and E. Wintermantel, Journal of Materials Science, Materials in Medicine 5 (1994), 481–484. The materials used were carbon fiber reinforced PEEK prepared by hot pressing. These composites contained approximately 60 vol % fibers and were sandblasted and then coated with a layer of hydroxyapatite 200 μm in thickness by plasma spraying. The authors of the paper report that carbon fibers in the outer layers of the composites were damaged in the plasma spraying process and that the adhesion between the plasma sprayed hydroxyapatite coating and the carbon fiber reinforced composite was very low.

Although a hydroxyapatite coating on a carbon fiber prosthesis would be desirable, the conventional plasma spraying techniques generally used for coating onto metals such as titanium cannot be used, because of the problems encountered as discussed above and, in particular, the degradation of the carbon fiber composite.

SUMMARY OF THE INVENTION

We have now developed a process for spraying hydroxyapatite or a modified hydroxyapatite onto a carbon fiber composite, such as a prosthesis, without degrading the composite.

Accordingly, the present invention provides a process for the coating of hydroxyapatite or a modified hydroxyapatite onto a carbon fiber composite which comprises carbon fibers bonded together with a polymeric material, which process comprises positioning the carbon fiber composite in a chamber maintained at a reduced pressure of from 25,000 to 10,000 Pa (250 to 100 mBar), and plasma spraying non-agglomerated hydroxyapatite or a non-agglomerated modified hydroxyapatite onto a surface of the carbon fiber composite whilst cooling the said surface of the composite with an inert liquid coolant medium.

DETAILED DESCRIPTION OF THE PREFERRED EMBODIMENTS

By the term "non-agglomerated" as used herein is meant that the particles of the hydroxyapatite or modified hydroxyapatite are essentially individual particles and do not form clumps or clusters.

In carrying out the process of the present invention the carbon fiber composite will generally be rotated and the speed of rotation will have an effect upon the cooling of the composite by the coolant medium. Preferably the composite is rotated at from 200 to 240 revolutions per minute, more preferably at from 210 to 220 revolutions per minute. If the composite is of a non-uniform shape and is not symmetrical about the axis of rotation then it may be necessary for the composite to rotate at a variable speed in order to ensure uniformity of thickness of the hydroxyapatite or modified hydroxyapatite coating. Alternatively, for some composite configurations it may be possible to move the plasma spraying torches, rather than to rotate the composite.

The plasma spraying is carried out in a chamber maintained at a reduced pressure of from 250 to 100 mBar, preferably 175 to 125 mBar, more preferably at about 150 mBar.

The plasma spraying is carried out using plasma spray torches which are generally operated using helium, neon, argon or nitrogen as the primary gas which is ionized to form the plasma, more preferably argon. The primary plasma forming gas may be admixed with a secondary plasma forming gas, such as a mixture of argon and hydrogen, for example Hytec 17 (Air Products & Chemicals Corporation).

The carbon fiber composite which is coated according to the process of the present invention comprises carbon fibers bonded together with a polymeric material such as polybutyleneterephthalate.

In carrying out the process of the present invention the liquid coolant medium is preferably liquid carbon dioxide, although other inert liquid coolant medium may also be used. The liquid coolant medium is preferably sprayed onto the rotating composite prosthesis from one or more nozzles positioned within the chamber such that the jets issuing from the nozzles impinge on the rotating composite prosthesis at an angle of from 15° to 30° to the horizontal, more preferably at an angle of about 22° to 26° to the horizontal. The nozzles are preferably placed at a distance of from 76 to 125 mm from the rotating composite, more preferably at a distance of about 100 mm from the composite.

The non-agglomerated hydroxyapatite or non-agglomerated modified hydroxyapatite which is coated onto the carbon fiber composite in accordance with the process of the present invention is in the form of a free flowing powder, preferably having a particle size of below 150 micrometers, more preferably in the range of from 110 to 130 micrometers.

The amount of coolant which is sprayed onto the composite will depend upon factors such as the speed of rotation of the composite, the melting point of the plastics material which bonds the carbon fibers together and the distance of the spray nozzles from the composite. Typically a temperature of about 200° C. or below at the surface of the composite will be maintained when the plastics material bonding the carbon fibers together is polybutylene terephthalate. The amount of coolant will thus be adjusted as required to maintain the desired temperature The coating of the non-agglomerated hydroxyapatite or non-agglomerated modified hydroxyapatite deposited according to the process of the present invention is preferably from 50 to 100 micrometers in thickness, more preferably from 50 to 90 micrometers in thickness.

The present invention includes within the scope a carbon fiber composite which has been coated with non-agglomerated hydroxyapatite or a non-agglomerated modified hydroxyapatite by the above described process.

The process of the present invention is of particular utility for the coating of prostheses. Whilst any prosthesis based on carbon fibers may be coated using the process of the present invention, the preferred composite is a cup or stem for a hip prosthesis or a knee prosthesis. The inside articulating surface of the cup is preferably coated with an ultrahigh molecular weight polyethylene prior to the coating of the composite with non-agglomerated hydroxyapatite or modified hydroxyapatite. The outer coated surface of the composite prosthesis is inserted in use in the desired location in the patient and a boney ingrowth into the hydroxyapatite coating ensues because of the biocompatible characteristics of the coating. In this manner the implant becomes fixed in position and the joint which has been replaced regains its strength.

An advantage of hydroxyapatite coated carbon fiber composite prostheses as compared to hydroxyapatite coated metal based prostheses is that the carbon fiber composite does not require any pretreatment to key or roughen the surface prior to coating since the first molten hydroxyapatite particles contained in the plasma stream which contact the carbon fiber composite melt the surface of the composite locally and thereby become bonded into the composite. This is in contrast to metal based prostheses which require a surface roughening treatment prior to coating such as a grit blasting treatment. The complete removal of residual particles of grit following a grit blasting operation is difficult. It will be appreciated, however, that any residual grit particles left on the metal surface prior to coating can cause problems such as inflammation of the joint when it is implanted into a patient and thus a coating technique which does not require such a pretreatment is advantageous.

Although the process of the present invention is of particular importance for the coating of prostheses, it may also be used to coat other articles such as carbon fiber composite plates with non-agglomerated hydroxyapatite or modified hydroxyapatite.

The present invention will be further described with reference to the following Examples.

EXAMPLE 1

A carbon fiber reinforced polybutyleneterephthalate cup, as described in EP-A-0552949, of internal diameter 45 mm and outer diameter 54 mm coated on the inside with a coating of ultrahigh molecular weight polyethylene was plasma coated with non-agglomerated hydroxyapatite having a particle size of from 30 to 110 micrometers according to the following procedure.

The outer surface of the composite was coated to a thickness of 60 micrometers according to the technique as described above. The surface which had been coated had a white appearance and the coating appeared to be reasonably uniform without any major surface defects.

The hydroxyapatite coated composite prepared by the above process was prepared for microscopical examination by mounting it with an epoxy resin and cross-sectioning.

The hydroxyapatite was injected into the plasma stream of a plasma gun through an inner feeder inside the anode of the gun. This technique allows the use of a less energetic and shorter flame, so decreasing the risk of thermal damage of the cup. A pressure of 150 mBar was maintained within the coating chamber. The carbon fiber reinforced cup was rotated at a speed of 210 rpm and liquid carbon dioxide sprayed onto the cup as a continuous jet in a total amount of 4 kg/cup. The coating procedure was for a total period of time of 150 seconds/cup in three operations. After each spraying operation the carbon fiber reinforced cup was allowed to cool for 8 to 10 seconds. After the total spraying operation the three separately coated layers were indistinguishable.

On examination no damage of the carbon fiber material had resulted from the plasma deposition of the hydroxyapatite. The average thickness of the hydroxyapatite coating layer was determined by examination of the mounted samples at 100×magnification and was determined to be about 60 micrometers in thickness.

EXAMPLE 2

An investigation was carried out of the bond of strength of hydroxyapatite to carbon fiber reinforced polybutyleneterephthalate (CFRPBT) in the form of flat plates as compared to hydroxyapatite coated stainless steel plates. Both the CFRPBT and the stainless steel plates were coated with hydroxyapatite to a thickness of about 60 micrometers. The steel plates were subjected to a grit blasting treatment prior to coating with the hydroxyapatite.

The CFRPBT and steel plates were both subjected to scratch tests in which the coating is scratched with a 1 mm point of tungsten carbide by applying a predetermined pressure of 2N at a constant velocity. The movement was repeated several times in a single direction.

The results obtained with the scratch coating applied to both the CFRPBT and steel plates showed a similar rate of removal of the coating of about 1 micrometer thickness per scratch. The coating on the stainless steel was removed at the same rate throughout the test, whereas it became harder to remove the coating from the CFRPBT near to the substrate. These results demonstrate the "chemical" nature of the bond between hydroxyapatite and the carbon fiber composite as compared to the bond formed on the stainless steel plates.

EXAMPLE 3

An investigation was carried out to determine the adhesion and mechanical resistance of hydroxyapatite coated carbon fiber reinforced polybutyleneterephthalate (CFRPBT) discs as compared to hydroxyapatite coated stainless steel plates.

CFRPBT discs, 30 mm diameter and 2.5 mm thickness, were vacuum plasma spayed with hydroxyapatite to a thickness of 60 micrometers according to the process as described in Example 1. Stainless steel plates, 2mm thick, were coated with hydroxyapatite to a thickness of 60 micrometers according to the same process.

The coated samples were then subjected to an impact test by dropping a 1 kilogram weight having a ball 12 mm in diameter at the bottom of the weight from a height of 15 cm onto the test surfaces. The deformation of the plates was caused by the impact of the ball on the surfaces thereof. The impact marks on the CFRPBT coated disc and on the coated stainless steel plates were inspected visually.

It was determined that the stainless steel plates deformed and the coatings flaked. The hydroxyapatite coated CFRPBT discs did not deform and the impact marks were scarcely visible. The coatings did not show any signs of flaking.

EXAMPLE 4

An investigation was carried out to determine the adhesion and mechanical resistance of a hydroxyapatite coating on CFRPBT by means of a tensile bond test.

CFRPBT discs, 30 mm diameter and 2.5 mm thickness were vacuum plasma sprayed with hydroxyapatite to a thickness of 60 micrometers according to the process a described in Example 1.

Coated and non-coated CFRPBT discs were glued between two pull-off tensile test samples of titanium and stainless steel. The non-coated CFRPBT samples were sandblasted on one side and this side was glued in each case to the titanium tensile bond test samples. For the coated CFRPBT discs, one coated side was glued in each case to the titanium tensile bond test samples and the moulded side to the stainless steel test samples.

The glue which was used was an epoxy adhesive 2214-Regular from 3M.

The samples were placed in a tensile tester DS-Europe operating with a load cell type LC 160 (Maximum load 1000 kg).

The following results were obtained:

Non-coated discs—Average 21.16 MPa.

Coated discs—Average 17.59 MPa.

Visual inspection of the broken parts for the non-coated and coated discs showed that all of the discs broke in the middle of the CFRPBT.

In conclusion, the interfaces CFRPBT/HA/titanium and CFRPBT/stainless steel are stronger than the tensile strength of the CFRPBT itself.

I claim:

1. A carbon fiber composite coated with a coating selected from the group consisting of hydroxyapatite and modified hydroxyapatite which coated composite has been produced by a process which comprises positioning the carbon fiber composite in a chamber maintained at a reduced pressure of from 25,000 to 10,000 Pa, and plasma spraying a coating onto a surface of the carbon fiber composite whil cooling the said surface of the composite with an inert liquid coolant medium, the said coating composition being selected from the group consisting of non-agglomerated hydroxyapatite and non-agglomerated modified hydroxyapatite.

2. A composite according to claim 1 wherein the composite is rotated at from 200 to 240 revolutions per minute during the coating process.

3. A composite according to claim 1 wherein the composite is rotated at from 210 to 220 revolutions per minute during the coating process.

4. A composite according to claim 1 wherein during the plasma spraying of the coating, argon is used as a primary gas.

5. A composite according to claim 1 wherein the plasma spraying of the coating is carried out in a chamber maintained at a reduced pressure in the range of from 17,500 to 12,500 Pa.

6. A composite according to claim 1 which composite comprises carbon fibers bonded together with polybutyleneterephthalate.

7. A composite according to claim 1 wherein the inert liquid coolant medium used during the coating process is liquid carbon dioxide.

8. A composite according to claim 7 wherein the liquid carbon dioxide is sprayed onto the rotating composite during the coating process.

9. A composite according to claim 7 wherein during the coating process the liquid carbon dioxide is sprayed onto the composite which is rotating from one or more nozzles positioned within the chamber, jets of coolant from the nozzles impinging on the composite at an angle of from 15° to 35° to the horizontal.

10. A composite according to claim 7 wherein during the coating process the liquid carbon dioxide is sprayed onto the composite which is rotating from one or more nozzles positioned within the chamber, the said nozzles being positioned at a distance of from 75 to 124 mm from the rotating composite.

11. Composite according to claim 1 wherein the said coating is from 50 to 100 micrometers thick.

12. Composite according to claim 1 which is selected from the group consisting of a cup for a hip prosthesis, a cup for a knee prosthesis, a stem for a hip prosthesis and a stem for a knee prosthesis.

* * * * *